United States Patent [19]

Fincke et al.

[11] Patent Number: 5,330,526
[45] Date of Patent: Jul. 19, 1994

[54] COMBINED DEFIBRILLATION AND PACING ELECTRODE

[75] Inventors: Randall W. Fincke, Winchester; Rolf S. Stutz, Cambridge, both of Mass.

[73] Assignee: ZMD Corporation, Wilmington, Del.

[21] Appl. No.: 877,838

[22] Filed: May 1, 1992

[51] Int. Cl.$^5$ ............................................. A61B 5/0402
[52] U.S. Cl. ...................................... 607/142; 607/152
[58] Field of Search ......................... 128/639, 640, 798

[56] References Cited

U.S. PATENT DOCUMENTS

| | | | |
|---|---|---|---|
| 4,391,278 | 7/1983 | Cahalan et al. | 128/798 |
| 4,538,612 | 9/1985 | Patrick, Jr. | 128/639 |
| 4,926,878 | 5/1990 | Snedeker | 128/798 |
| 4,989,607 | 2/1991 | Keusch et al. | 128/798 |

Primary Examiner—William E. Kamm
Assistant Examiner—Scott M. Getzow
Attorney, Agent, or Firm—Fish & Richardson

[57] ABSTRACT

An electrode for transcutaneously delivering defibrillation pulses to a patient's heart. The electrode comprises an insulating substrate, a conducting plate which is positioned on the substrate and which has an electrical terminal for making a connection to an external source of electrical current, and a layer of electrolytic gel covering the entire top surface of the conducting plate. This gel contacts a patient's skin when the electrode is positioned on the skin to prevent the conducting plate from contacting the skin. The gel comprises a concentration of an electrolyte such that the combination series resistance of two of the electrodes, when measured with the electrodes configured in a series circuit with a 50 Ω resistance, and with the electrolytic gel layer of each electrode in contact with that of the other electrode, is greater than 1 Ω when a 200 Joule defibrillation pulse is discharged into the series circuit.

42 Claims, 2 Drawing Sheets

COMBINED DEFIBRILLATION AND PACING ELECTRODE

BACKGROUND OF THE INVENTION

This invention relates to electrodes used in transcutaneous cardiac defibrillation and pacing procedures.

Transcutaneous cardiac defibrillation is an emergency procedure for treating ventricular fibrillation, a condition in which the electrical pulse generators in the cardiac muscle fibrillate asynchronously, causing chaotic muscle contraction. In the procedure, a high energy electrical pulse, called a defibrillation pulse, is transcutaneously delivered to a patient's fibrillating heart to resynchronize the heart's pulse generators. In transcutaneous cardiac pacing, pacing stimuli are transcutaneously delivered to a patient's heart to continuously pace the heart.

Defibrillation pulses and pacing stimuli are transcutaneously delivered from pulse generation equipment to a patient via a pair of electrodes applied to the patient's thorax in a suitable configuration. Typically, either of two types of electrodes is used; the first type comprises separate, dedicated defibrillation and pacing electrode pairs, while the second comprises a multifunction electrode pair which supports both defibrillation and pacing procedures.

The multifunction electrode typically consists of a flexible adhesive substrate, supporting a conducting plate, which is temporarily affixed to the patient's skin, and so does not require an operator to forcibly hold it in place on the skin. This electrode is designed to be used for one treatment session and then discarded.

It is desirable to provide a uniform contact surface between the multifunction electrode conducting plate and the patient's skin. To this end, a water-based electrolytic gel is typically provided on the electrode conducting surface. With the electrode in place on the patient's thorax, this gel soaks the skin, allowing the electrolytes in the gel to permeate the skin and thereby provide a good conducting path for the defibrillation and pacing stimuli. In addition, the gel wets hair on the patient's skin and provides a good conductive path around the hair and into the skin. The electrodes are typically gelled during the manufacturing process and require no further preparation before use.

Conventionally, the components of the aqueous electrolytic gel are chosen to achieve very low gel resistance, and thus very high gel conductivity, to minimize the pulse energy dissipated in the gel and thereby maximize the defibrillation pulse energy and pacing stimulus delivered to the patient. The electrical resistance of a patient's thorax is believed to range somewhere between 25 Ω and 100 Ω, and is typically modelled as 50 Ω; the series resistance of the pair of multifunction electrodes, including electrode gel, is held below 1.0 Ω.

In defibrillation procedures, typically more than one defibrillation pulse is required to successfully defibrillate a patient's heart. Being affixed to the patient's skin at the start of a defibrillation session, multifunction electrodes do not change position with each pulse application. It has been clinically observed that with repeated defibrillation pulse applications, some burning of a patient's skin may occur at the perimeter of the gel layer of each of the multifunction electrodes. This burning is characterized by erythema across a thin band at the gel perimeter location. It is believed that the location of the burn is determined by the spatial distribution of the defibrillation pulse current across the electrode and gel face; this current is highest at the perimeter of the gel, due to the abrupt boundary of the electric field at this perimeter. The electrode burn is exacerbated by repeated defibrillation pulses because the multifunction electrodes are maintained in a fixed position throughout a pulse series.

In conventional transcutaneous pacing procedures, the patient may experience a stinging of the skin in the area of the electrodes' positions. This stinging is believed to also be related to the high current level of delivered stimuli at the edge of the conducting plate and gel.

SUMMARY OF THE INVENTION

In general, the invention features increasing the resistance of electrodes used for transcutaneously delivering defibrillation pulses to the heart, and thereby decreasing the potential for burning of the skin during the defibrillation. The electrode comprises an insulating substrate, a conducting plate which is positioned on the substrate and which has an electrical terminal for making a connection to an external source of electrical current, and a layer of electrolytic gel covering the entire surface of the conducting plate. This gel contacts a patient's skin when the electrode is positioned on the skin to prevent the conducting plate from contacting the skin. The gel comprises a concentration of an electrolyte such that the combination series resistance of two of the electrodes, when measured with the electrodes configured in a series circuit with a 50 Ω resistance, and with the electrolytic gel layer of each electrode in contact with that of the other electrode, is greater than 1 Ω when a 200 Joule defibrillation pulse is discharged into the series circuit. The invention provides an electrode gel resistance which is high enough to significantly decrease the potential for burning of a patient's skin at the perimeter location of the electrodes on the skin (by comparison to the burning associated with conventional disposable electrodes); at the same time, the gel resistance is low enough that only an insignificant percentage of the defibrillation pulse is dissipated in the gel resistance.

In preferred embodiments, the combination series resistance of two of the electrodes is at least 1.5 Ω, but not more than 5 Ω. In more preferred embodiments, the combination electrode series resistance is at least 1.5 Ω but not more than 3 Ω.

In preferred embodiments, the electrode is configured to deliver transcutaneous pacing stimuli, in addition to defibrillation pulses. The increased electrode gel resistance decreases the current density of pacing pulses at the perimeter of the electrode, thereby reducing the skin stinging typically associated with conventional transcutaneous pacing electrodes. In addition, the pacing and defibrillation multifunctionality of the electrode provides great efficiency in emergency medical equipment and procedures. Preferably, the electrode comprises a front electrode to be positioned on the front of a patient's chest and a back electrode to be positioned on the back of a patient's chest, and the conducting plates of the front and back electrodes are at least 8 square inches.

In other preferred embodiments, the front and back electrode conducting plates each comprise a geometry which occupies a general region but which spans a geometric area less than that of the general region, and which has a perimeter which is greater than the perimeter of the region. Preferably, the front and back electrode conducting plates each comprise a geometry including inwardly extending excursions of the perimeter of the geometry at spaced intervals around the geometry perimeter; more preferably, the front electrode conducting plate occupies a generally circular region and the back electrode conducting plate occupies a generally rectangular region. The increased perimeter of the conducting plates' geometries works in concert with the increased resistance of the gel to decrease the current delivered at the perimeter of the plates and thereby decrease the stinging of transcutaneous pacing stimuli.

Other features and advantages of the invention will become apparent from the following description of the preferred embodiment of the invention and from the claims.

DESCRIPTION OF THE PREFERRED EMBODIMENT

Figure 1:
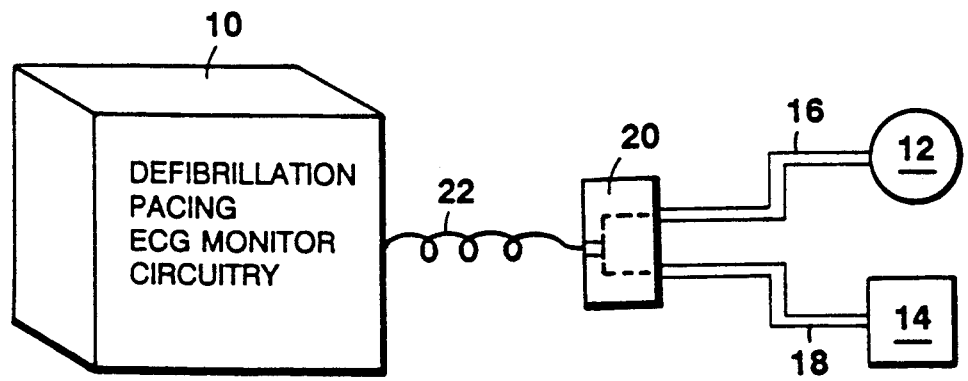
FIG. 1 is a perspective view of a portable defibrillation and pacing unit connected to the electrodes of the invention.

Referring to FIG. 1, there is shown a portable defibrillation and pacing unit 10 which includes electrical circuitry needed for generating electrical signals used in emergency defibrillation, pacing, and ECG monitoring procedures. Such a unit is available from Zoll Medical Corporation of Woburn, Mass., under the product name PD1400, as well as product names. A pair of disposable multifunction electrodes 12, 14 are connected to the defibrillation and pacing unit via corresponding electrode wires 16, 18, which are coupled in a multifunction connector 20 to a cable bundle 22, ending in an electrical connection with the defibrillation and pacing unit.

In operation, the multifunction electrodes 12, 14 are affixed to the front and back of the patient's chest in a position aligned with the patient's heart. As described below, the adhesive property of the electrodes provides for them to remain in position without manual effort. If the patient requires cardiac pacing, the defibrillation and pacing unit is programmed to initiate and maintain appropriate pacing stimuli, which are transcutaneously delivered to the patient's heart. If the patient alternatively or additionally requires cardiac defibrillation, the defibrillation and pacing unit is programmed to discharge a defibrillation pulse, typically having a peak energy in the range of 200–400 Joules. Based on the cardiac response of the patient to the defibrillation pulse, additional defibrillation pulses may be applied to the patient. Throughout the delivery of any cardiac pacing and defibrillation pulses, the electrodes 12, 14 remain intact on the patient's thorax.

Figure 2A:
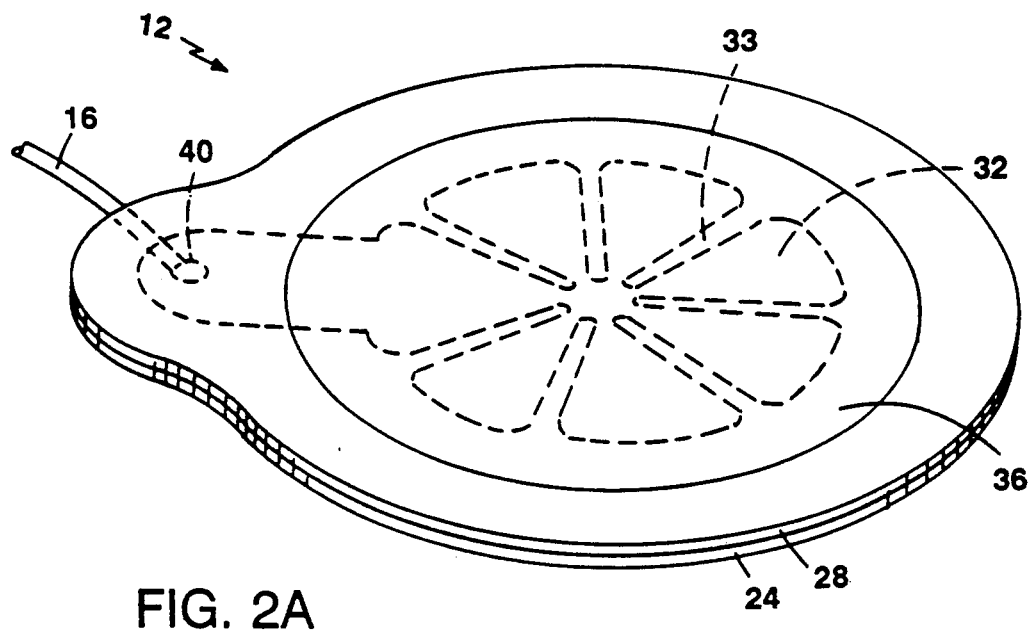
FIG. 2A is another perspective view of the front electrode shown in FIG. 1.
Figure 2B:
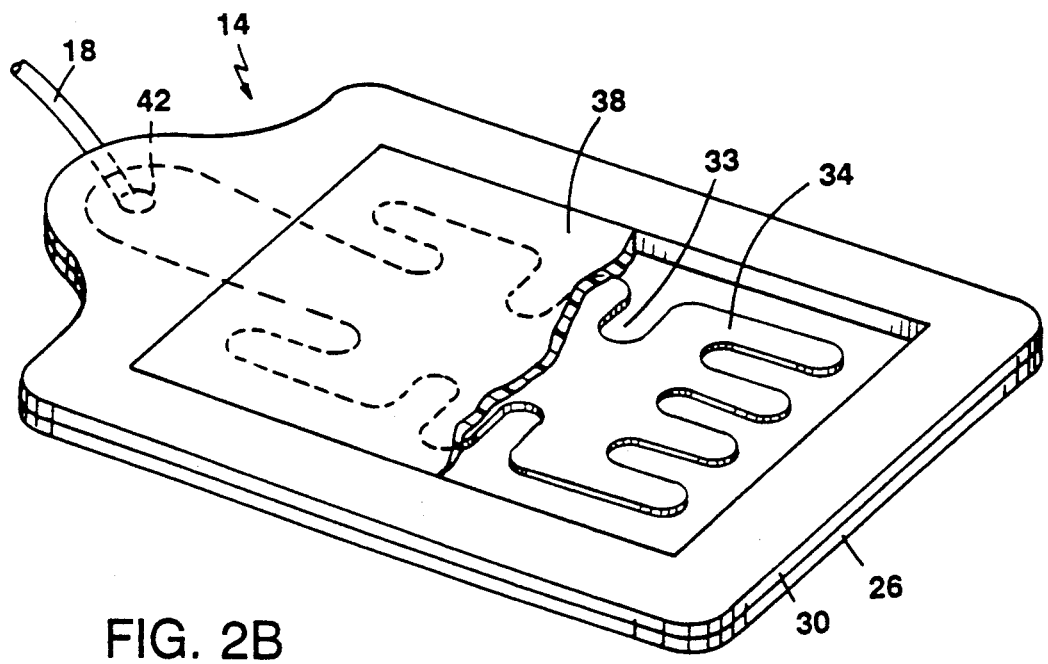
FIG. 2B is another perspective view of the back electrode shown in FIG. 1.

Referring to FIGS. 2A and 2B, illustrating the front and back multifunction electrodes 12, 14, respectively, in more detail, the two electrodes are identical except for their lateral shapes. The front electrode 12 is round, for easy placement on the chest area of a patient's thorax, while the back electrode 14 is rectangular, for easy alignment with the spine on the back area of the patient's thorax. An insulating base layer 24, 26 of each electrode is composed of a layer of flexible, closed cell-type polyethylene foam tape. The flexibility of the tape allows it to conform to the contours of a patient's thorax when the electrodes are affixed to the thorax. While other types of base layer materials are acceptable, the base material must be of a high enough density to provide a liquid barrier to aqueous gel so as to hold the gel on one side of the electrode, as described below, and must have excellent compressibility qualities.

The dimensions of the foam base layer are determined based on physiological considerations for both transcutaneous pacing and defibrillation. The area of the electrodes' conducting plates, which are smaller than the corresponding base layers, must be larger than that of the heart; cardiac defibrillation is not effective unless the entire heart is in effect "covered" by a defibrillation pulse. Other considerations for pacing and defibrillation are described below. In addition, the base layer dimensions are here chosen to provide some amount of area surrounding the conducting plates for adhesion to a patient's thorax. The Association for the Advancement of Medical Instrumentation (AAMI) specifies that the smallest adult defibrillation conducting plate may be 8 square inches. Thus, any area at least this large would be acceptable in theory for the insulating base layer. Here the front electrode 12 has a round foam base of 6 inches in diameter, with a corresponding area of 28.3 in$^2$. The back electrode 14 has a rectangular foam base of 5 inches by 6.5 inches, with a corresponding area of 32.5 square inches. As explained below, these dimensions provide adequate mechanical support for the electrode conducting plates and space for adhesive support.

The thickness of the base layers is also determined based on physiological factors. A thin base layer easily conforms to the contours of a patient's thorax, while a thick base layer evenly supports the metal electrode and provides more even current distribution across the electrode. A trade-off must be made between these two opposing considerations. Here, the foam base layer of each of the electrodes is ⅛ inch-thick; other thicknesses may be used based on particular situations.

Supported by the foam base layers 24, 26 are peripheral foam frames 28, 30, respectively, which border conducting plates 32, 34, sandwiched between the foam base layers 24, 26 and upper gel-filled layers 36, 38, respectively. The frames provide mechanical support at the periphery of the electrode assembly and define an inner well in which the conducting plates and gel-filled layers are positioned. The front electrode foam frame 28 is 1 inch-wide, defining an inner well of 12.3 square inches; the back electrode foam frame 30 is 0.8 inches-wide, defining an inner well of 17.5 square inches. Each of the foam frames 28, 30 comprise the same polyethylene foam tape as the base layers. These foam frames are 1/16 inch-thick; other thicknesses may be used based on particular situations. The foam frames are affixed to the bottom foam layers with hot melt all-purpose glue.

The top surface of each of the foam frames is coated with a hypoallergenic medical grade acrylic adhesive designed for use on human skin. This adhesive provides the mechanism for temporarily affixing the electrodes in position on a patient's thorax. Using this adhesive, no additional adhesive or any manual force is required to maintain the electrodes in position during delivery of electrical signals to a patient.

The electrode conducting plates 32, 34 located in the wells defined by the foam frames, are of a geometry selected for promoting even distribution of electrical current across the area of the electrodes. Here, the front electrode conducting plate 32 is generally circular (occupies a generally circular region) but includes inwardly extending excursions 33 of the perimeter. Likewise, the back electrode conducting plate 34 is generally rectangular and also includes inwardly extending excursions 33 of the perimeter. These inward excursions are about one third as long as the diameter of the electrode (or in the case of the rectangular electrode, one third the transverse dimension). Less of an inward excursion may be used; preferably the excursion is at least one fifth of the transverse dimension of the conducting plate. This type of geometry is chosen to increase the conducting plate perimeter beyond that which would be obtained using a continuous geometry. The increased perimeter of the conducting plate works in concert with the increased gel resistance to decrease the stinging of skin typically associated with transcutaneous pacing; the longer the perimeter for a given conducting plate geometry, and the higher the resistance of the gel, the more comfortable the pacing stimuli are to a patient. In addition to this geometric feature, neither of the conducting plate geometries includes a point or corner. This eliminates discontinuities, at which a high electric field, and correspondingly high current density, could be generated. Each of the conducting plates terminates ¼ inch from the edge of the foam frame border, and therefore is ¼ inch smaller than the layer covering it, as described below. Other conducting plate geometries, including a continuous geometry, may alternatively be used.

As mentioned previously, the dimensions of the conducting plates must meet a requirement for being large enough to defibrillate the heart. A larger size conducting plate, as opposed to a smaller conducting plate, is also desirable because for a given defibrillation current pulse, the larger plate decreases the current amplitude at the edge of the plate (compared to a smaller plate), and thereby decreases the potential for burning associated with that current amplitude. In addition, the larger the electrode conducting plate, the more likely are pacing stimuli to capture, and thereby pace, some of the cardiac pacing cells. Conversely, the smaller the electrode conducting plate, the more effective it is at pacing cardiac pacing cells it does capture, because the pacing current is increased in a smaller area, which more effectively stimulates the pacing cells. Based on all of these considerations, the front electrode conducting plate 32 here spans an area of 8.4 square inches and the back electrode conducting plate 34 spans an area of 11.7 square inches, both conducting plate areas being in conformance with the AAMI minimum conducting plate area requirement of 8 square inches, and optimizing the size for cardiac pacing procedures.

Both conducting plates are composed of a 0.001 inch-thick layer of tin laminated to a 0.006 inch-thick layer of Tyvek. Having a total thickness of 0.007 inches, the electrodes are radio-translucent. Thus an x-ray taken of the thorax region of a patient with the electrodes affixed to his thorax will be only minimally shadowed by the presence of the electrodes. This is particularly important because frequently a patient having recurring cardiac distress will require cardiac pacing or defibrillation during a session to take an x-ray. If such a provision for radio-translucency is not required, the conducting plate may be of some higher thickness, and may also comprise some other good conducting material. For example, a thicker conducting plate would provide good mechanical qualities, but would not be as radio-translucent as a thinner electrode.

Each conducting plate 32, 34 includes an extension area 40, 42, respectively, which extends laterally beyond the layer covering the plate but which is itself covered by the foam frame border 28, 30, respectively. Each foam border is correspondingly extended in the location of the conducting plates' extension areas. It is at the extension areas 40, 42 that the conducting plates are electrically connected to corresponding electrical wires 16, 18 for connection back to the portable pacing and defibrillation unit. This connection is here made using a rivet technique, but other techniques are also feasible. The electrical wires 16, 18 are 20 gauge and rated for 10 KV to adequately support high energy defibrillation pulses. They comprise copper wire insulated with a PVC coating.

Each conducting plate 32, 34 is positioned tin side up within the foam well. It is completely covered by a corresponding reticulated open cell-type gel foam layer 36, 38 designed to support an amount of aqueous electrolytic gel. The front electrode gel foam layer 36 is circular, having a diameter of 3.95 inches and an area of 12.3 square inches. The back electrode gel foam layer 38 is rectangular, having sides 3.5 inches by 5 inches and an area of 17.5 square inches. Thus, gel foam layers 36, 38 fit exactly within the windows defined by the outer foam borders 28, 30.

The gel foam layers 36, 38, like the conducting plates 32, 34 under them, may comprise a geometry which maximizes the gel perimeter for a given general shape. For example, the front electrode gel foam layer 36 may include excursions 33 to thereby increase the layer perimeter beyond that which a simple circle would provide. This design could be used with the front conducting plate 32 having excursions 33 as shown, or with a simple circular plate. An increased gel layer perimeter decreases the level of current delivered to the patient at the perimeter; this decreased current correspondingly decreases the potential for burning associated with the electrode during defibrillation.

Each gel foam layer 36, 38 is 3/16 inch-thick. Because the wells defined by outer foam borders 28, 30 are ⅛ inch-thick, the gel foam layers 36, 38 protrude above the foam borders 28, 30 by 1/16 inch. This additional gel foam thickness ensures that very good contact is made to a patient's skin when the electrodes are affixed to the skin. With the stated areas and thickness, the front gel foam layer 36 has a gel space capacity of 37.5 cm$^3$ and the back gel foam layer 38 has a gel space capacity of 32.5 cm$^3$.

The gel which is supported by the gel foam layers 36, 38 is a viscous, clear, aqueous electrolytic gel composed of a polymer, a surface active agent, a corrosion inhibitor, a salt, here sodium chloride, preservatives, and purified water. It has a pH between 5 and 6. The front electrode's gel foam layer 36 is filled with 33 grams of the gel, which fills the layer to 88% of its capacity. The back electrode's gel foam layer 38 is filled with 47 grams of the gel, which fills the layer to 87% of its capacity. The gel-soaked foam layers 36, 38 completely wet and cover the underlying metal conducting plates; this is important for avoiding direct contact of the plates to a patient's skin when the electrodes are in position on a patient, a situation which could cause discomfort. The electrodes' foam base layers 24, 26, being quite dense, prevent the gel from penetrating under the conducting plates and through the base to the outer back side of the base layers, and thereby prevent any accidental electrical shock to a medical operator.

The sodium chloride (NaCl) concentration of the gel determines the electrical resistance of the gel. The lower the NaCl concentration, the higher the resistance of the gel. This resistance dissipates some of the energy in the electrical pulse signals delivered to the electrodes from the signal generation equipment, and thereby decreases the pulse energy ultimately delivered to a patient. The AAMI specifies that the defibrillation pulse energy delivered to a 50 $\Omega$ resistive load, the typical resistance of a patient's thorax, must be within 4 Joules or +/- 15%, whichever is greater, of the pulse energy generated by the electrical signal generation equipment. Thus, for a defibrillation pulse energy specified to be 200 Joules, the pulse energy reaching a patient through the electrodes must be between 170 and 230 Joules. The AAMI also specifies that the peak current of a 360 Joule defibrillation pulse delivered to a 50 $\Omega$ resistive load must be between 45 and 66 Amps.

Fundamentally, and in addition to these considerations, the electrolyte concentration, and correspondingly the resistance, of the gel is chosen based on a desire to eliminate the potential for burning of a patient's skin at the perimeter of the electrodes during defibrillation, and to decrease the discomfort typically associated with transcutaneous pacing. The burning is caused by the nonuniform distribution of current across the conducting plates; the current is highest at the perimeter of a conducting plate, due to the abrupt boundary of the electric field at this perimeter. Thus, a reduction in the defibrillation current density at the plate and gel edge results in a decrease in the potential for burning of a patient's skin. Similarly, a decrease in the level of pacing stimuli at the plate perimeter makes transcutaneous pacing more comfortable for a patient. While NaCl is the electrolyte used here, other salts may alternatively be used which would exhibit similar conductivity and impedance characteristics.

Figure 3:
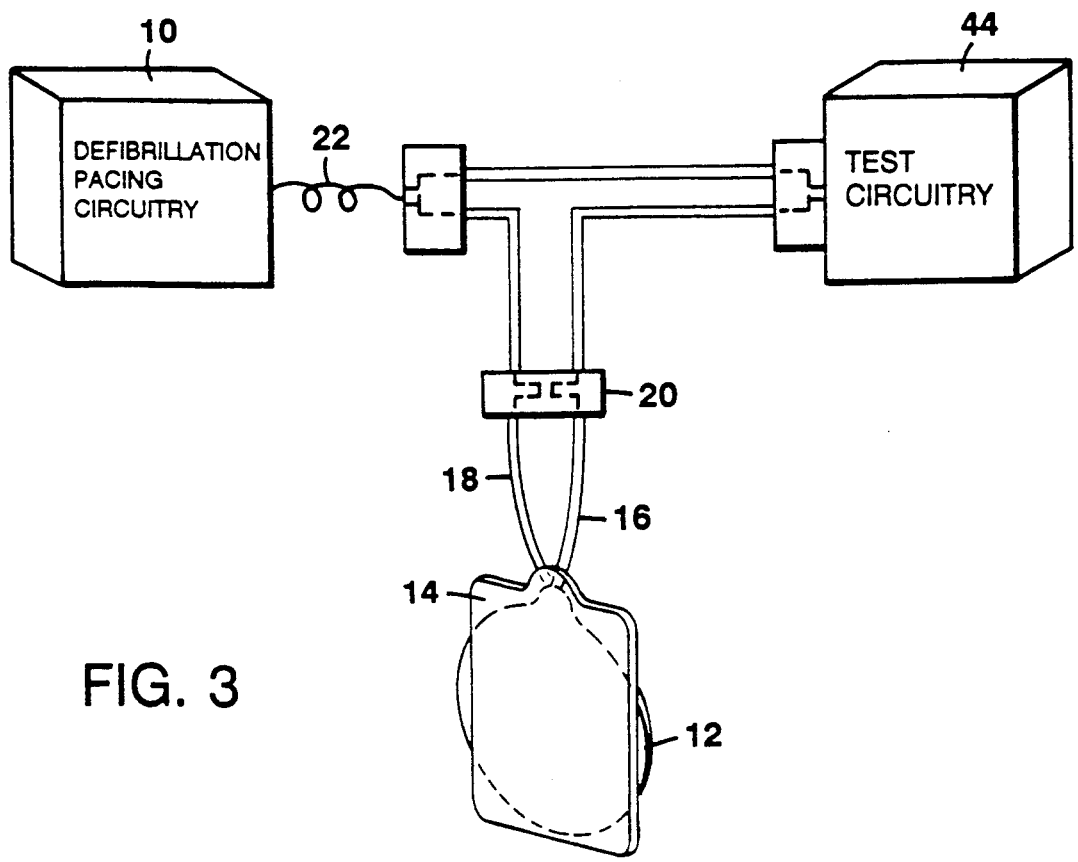
FIG. 3 is a schematic of a testing circuit for measuring the resistance of the electrodes shown in FIG. 1.

The gel's NaCl concentration and corresponding gel resistance is here chosen to be somewhere in the range which meets the AAMI defibrillation standards requirements and which provides the physiological benefits described above. To accurately determine the gel resistance as a function of NaCl concentration, the gelled electrodes are tested in the test setup illustrated in FIG. 3. In this configuration, the front electrode 12 is adhered to the back electrode 14, with the gel foam layers 36, 38 of the two electrodes facing and in contact with each other. The connecting wires 16, 18 of the two electrodes are connected via the multifunction connector 20 to the defibrillation and pacing unit 10 and a test circuit unit 44, for example, a Dynatech Impulse 3000 tester. A series loop is thus configured to consist of the defibrillation and pacing unit 10, the front electrode 12, the back electrode 14, and the test circuit unit 44. The test circuit unit 44 is configured to provide a resistive load, for example, 50 $\Omega$ resistor, simulating the resistive load of a patient's thorax, and corresponding measurement circuitry.

With a 200 Joule defibrillation pulse generated by the defibrillation circuit and the test circuit 44 configured to provide a 50 $\Omega$ resistive load, the following NaCl concentrations, specified in percent weight per volume, are shown to produce the corresponding resistance of the combination of the two electrodes in series, and the corresponding energy delivered to the load—a short circuit in place of the electrodes is used as the control:

| NaCl CONC. | ELECTRODE RESISTANCE | ENERGY DELIVERED |
| --- | --- | --- |
| 4.7% | 0.88 $\Omega$ | 204.59 Joules |
| 1.5% | 1.55 $\Omega$ | 202.58 Joules |
| 1.0% | 2.30 $\Omega$ | 200.21 Joules |
| Short | 0–0.005 $\Omega$ | 207.50 Joules |

In clinical tests of electrodes using gels of the 4.7%, 1.5%, and 1.0% NaCl concentrations, it is found that the physiological electrode edge burn of electrodes using either of the 1.5% and 1.0% NaCl concentration gels is dramatically reduced from that of the 4.7% NaCl concentration gel. In these two cases, skin at the perimeter of the electrodes is reddened after a defibrillation pulse application, but this redness is not as pronounced as that caused by the electrodes with the 4.7% NaCl, and more pulses must be applied before the skin is actually burned. Thus, the lower NaCl concentrations clearly aid in reducing burning caused by the electrodes. In addition, transcutaneous pacing using the lower NaCl-concentration gels is more comfortable, compared to a higher NaCl-concentration gel. An additional benefit of a reduced NaCl concentration in the electrode gel is a decrease in the corrosive tendencies of the conducting plate-gel configuration.

Considering the AAMI requirement for delivering within +/-15% of the energy of a generated defibrillation pulse to a 50 $\Omega$ load, all of the NaCl gels (4.7%, 1.5%, and 1.0%) meet this requirement; in fact, using the short circuit load test as a baseline, the three electrodes deliver at least 96.5% of the 200 Joule pulse to a 50 $\Omega$ load, for a maximum energy loss of only 3.5%. Based on these results, the 1.55 $\Omega$ electrode is preferred, but an acceptable range of possible resistances exists; the lower bound on resistance is set by the electrode burning phenomenon, and the upper bound is set by the loss of pulse energy into the resistive gel.

The final components of the electrodes are plastic covers (not shown) for protecting the electrode assemblies during storage. The covers comprise 10 mil-thick sheets of natural styrene coated with a layer of thermal cured silicone; this layer faces the gel foam when correctly positioned. The shape and size of each cover is identical to the foam base layer of the corresponding electrode. The covers are contoured to accommodate the 1/16 inch protrusion of the gel foam layer above the rest of the electrode surface.

In assembly of the multifunction electrode pair, the gel foam layers are first positioned within their corresponding foam frames, and the conducting plates are riveted to corresponding connection wires and positioned under the gel foam layers, with the tin side of the plates facing toward the gel foam layers. Then the foam border layers, with the gel foam layers and conducting plates in position, are glued to the corresponding foam base layer. Next the polymer gel is applied to the gel foam layers in the prescribed quantities. Finally, the styrene plastic covers are affixed on the gel foam side of the electrode assembly.

Other embodiments are within the scope of the invention. For example, the foam base and border pieces may together be an integral structure, rather than two separate pieces. The gel foam layer may comprise some other material or mechanism for supporting an electrolytic gel, or may provide for the application of gel before electrode use, rather than at the time of manufacture. Other electrolytic gels may be used in place of that described, and may be solid, rather than aqueous.

What is claimed is:

1. An electrode for transcutaneously delivering defibrillation pulses to a patient's heart, the electrode comprising:

an insulating substrate, a conducting plate having a top surface, a bottom surface, and an electrical terminal for making a connection to an external source of electrical current, said conducting plate being positioned with said bottom surface on said substrate, and a layer of electrolytic gel comprising a concentration of an electrolyte that produces a combination series resistance of two of said electrodes, when measured with the electrodes configured in a series circuit with a 50 Ω resistance, and with the electrolytic gel layer of each electrode in contact with that of the other electrode, that is greater than 1 Ω when a 200 Joule defibrillation pulse is discharged into the series circuit, said layer of electrolytic gel covering the entire top surface of said conducting plate, the gel contacting a patient's skin when the electrode is positioned on the patient's skin to thereby prevent said conducting plate from contacting the patient's skin.

2. The electrode of claim 1 wherein said combination series resistance is at least 1.5 Ω.

3. The electrode of claim 2 wherein said combination series resistance is not more than 5 Ω.

4. The electrode of claim 3 wherein said combination series resistance is not more than 3 Ω.

5. The electrode of claim 1 wherein said combination series resistance is at least 5 Ω.

6. The electrode of claim 1 wherein said combination series resistance is such that the energy of said defibrillation pulse discharged into said series circuit delivered to said 50 Ωresistance is within 30 Joules of the 200 Joule defibrillation pulse.

7. The electrode of claim 6 wherein said combination series resistance is such that the energy of said defibrillation pulse discharged into said series circuit delivered to said 50 Ω resistor is within 20 Joules of the 200 Joule defibrillation pulse.

8. The electrode of claim 1 wherein said electrode conducting plate occupies a general region having an area that is greater than the surface area of the electrode conducting plate and a perimeter that is less than the perimeter of the electrode conducting plate.

9. The electrode of claim 8 wherein said electrode is intended to be disposed of after use.

10. The electrode of claim 9 further comprising a removable insulating cover which when positioned on the electrode entirely covers the electrolytic gel layer, the cover designed to be removed from the electrode prior to use of the electrode.

11. The electrode of claim 1 wherein said electrolyte is a salt.

12. The electrode of claim 11 wherein said salt is sodium chloride.

13. The electrode of claim 12 wherein said layer of electrolytic gel is supported by a layer of foam covering the entire top surface of said conducting plate so that said foam contacts said patient's skin when the electrode is positioned on the skin, the foam being soaked with said electrolytic gel.

14. The electrode of claim 13 wherein said foam layer is at least 3/16 inch-thick.

15. The electrode of claims 1 or 14 wherein a portion of the substrate extending beyond the area of the conducting plate includes adhesive for temporarily affixing the electrode to a patient's skin.

16. The electrode of claim 15 wherein said adhesive comprises a medical grade acrylic adhesive.

17. The electrode of claim 15 wherein the area of the substrate extending beyond the area of the conducting plate comprises a boarder layer of flexible foam positioned on top of said substrate and encircling said conducting plate.

18. The electrode of claim 17 wherein the top surface of said border layer is coated with said adhesive for temporarily affixing the electrode to a patient's skin.

19. The electrode of claim 1 wherein said substrate has an area larger than the area of the conducting plate.

20. The electrode of claim 19 wherein said insulating substrate comprises a layer of flexible foam at least 1.8 inches-thick.

21. The electrode of claim 1 wherein the conductivity of said electrolytic gel is less than or equal to the conductivity of a gel comprising a sodium chloride concentration of 4.7% weight per volume of the gel.

22. The electrode of claim 21 wherein the conductivity of said electrolytic gel is less than or equal to the conductivity of a gel comprising a sodium chloride concentration of 1.5% weight per volume of the gel.

23. The electrode of claim 22 wherein said electrolytic gel is a water-based polymer gel.

24. A set of electrodes, each of said electrodes comprising:

an insulating substrate, a conducting plate having a top surface, a bottom surface, and an electrical terminal for making a connection to an external source of electrical current, said conducting plate being positioned with said bottom surface on said substrate, and a layer of electrolytic gel comprising a concentration of an electrolyte that produces a combination series resistance of two of said electrodes, when measured with the electrodes configured in a series circuit with a 50 Ω resistance, and with the electrolytic gel layer of each electrode in contact with that of the other electrode, that is greater than 1 Ω when a 200 Joule defibrillation pulse is discharged into the series circuit, said layer of electrolytic gel covering the entire top surface of said conducting plate, the gel contacting said patient's skin when the electrode is positioned on the patient's skin to thereby prevent said conducting plate from contacting the skin, said set of electrodes comprising a front electrode to be positioned on the front of a patient's chest and a back electrode to be positioned on the back of a patient's chest, the conducting plate of the front electrode having an area of at least 8 square inches and the conducting plate of the back electrode having an area of at least 8 square inches.

25. The set of electrodes of claim 24 wherein the shape of the perimeter of each of said electrode conducting plates is such that each said electrode conducting plate occupies a general region having an area that is greater than the surface area of the electrode conducting plate and a perimeter that is less than the perimeter of the electrode conducting plate.

26. The electrode of claim 25 wherein said front set of electrodes conducting plate occupies a generally circular region and said back electrode conducting plate occupies a generally rectangular region.

27. The electrode of claim 24 wherein said front set of electrodes conducting plate and said back electrode conducting plate each comprises a continuous geometry including inwardly extending excursions of the perimeter of said geometry at spaced intervals around the perimeter of said geometry.

28. The set of electrodes of claim 27 wherein each of said inward perimeter excursions extends into said geometry a distance of at least one fifth of the transverse dimension of said plate in the direction of said excursion.

29. The set of electrodes of claim 24 wherein said layer of gel of the front electrode has an area of at least 8 square inches and said layer of gel of the back electrode has an area of at least 8 square inches.

30. The set of electrodes of claim 29 wherein each of said layers of gel occupies a general region having an area that is greater than the surface area of the layer of gel and a perimeter that is less than the perimeter of the layer of gel.

31. The set of electrodes of claim 30 wherein said insulating substrate of said front electrode and said insulating substrate of said back electrode each has an area of at least 8 square inches.

32. A method of transcutaneously defibrillating a patient's heart, the method comprising the steps of:
generating an electrical defibrillation pulse, and
delivering said pulse to said patient through electrodes applied to said patient's thorax, the electrodes each comprising:
an insulating substrate,
a conducting plate having a top surface, a bottom surface, and an electrical terminal for making a connection to receive said electrical defibrillation pulse, said conducting plate being positioned with said bottom surface on said substrate, and
a layer of electrolytic gel comprising a concentration of an electrolyte that produces a combination series resistance of two of said electrodes, when measured with the electrodes configured in a series circuit with a 50 Ω resistance, and with the electrolytic gel layer of each electrode in contact with that of the other electrode, that is greater than 1 Ω when a 200 Joule defibrillation pulse is discharged into the series circuit, said layer of electrolytic gel covering the entire top surface of said conducting plate, the gel contacting a patient's skin when the electrode is positioned on the patient's skin to thereby prevent said conducting plate from contacting the patient's skin.

33. The method of claim 32 further comprising the steps of:
generating electrical pacing stimuli, and
transcutaneously delivering said electrical pacing stimuli to said patient's heart through said electrodes applied to said patient's thorax.

34. The method of claim 32 wherein said defibrillation pulse has an energy between 200 and 400 Joules.

35. The method of claim 32 wherein the difference between the energy of said defibrillation pulse delivered to said patient and the total energy of said defibrillation pulse is less than or equal to the larger of 10% of the total energy of said defibrillation pulse or 4 Joules.

36. The method of claim 35 wherein said difference is less than or equal to 10% of the total energy of said defibrillation pulse.

37. The method of claim 32 wherein said combination series resistance is at least 1.5 Ω.

38. The method of claim 37 wherein said combination series resistance is at least 5 Ω.

39. The method of claim 37 wherein said combination series resistance is not more than 5 Ω.

40. The method of claim 39 wherein said combination series resistance is not more than 3 Ω.

41. The method of claim 32 wherein the energy of said defibrillation pulse discharged into said series circuit delivered to said 50 Ω resistor is within 30 Joules of the 200 Joule defibrillation pulse.

42. The method of claim 41 wherein the energy of said defibrillation pulse discharged into said series circuit delivered to said 50 Ω resistor is within 20 Joules of the 200 Joule defibrillation pulse.

* * * * *